United States Patent
Masutani et al.

(10) Patent No.: US 11,321,836 B2
(45) Date of Patent: May 3, 2022

(54) IMAGE-PROCESSING DEVICE, IMAGE-PROCESSING METHOD, AND IMAGE-PROCESSING PROGRAM FOR SETTING CELL ANALYSIS AREA BASED ON CAPTURED IMAGE

(71) Applicants: NIKON CORPORATION, Tokyo (JP); The University of Tokyo, Tokyo (JP)

(72) Inventors: Mamiko Masutani, Yokohama (JP); Kenta Imai, Chigasaki (JP); Wataru Tomosugi, Yokohama (JP); Takuro Saigo, Tokyo (JP); Chisako Iwamoto, Yokohama (JP); Masafumi Yamashita, Fujisawa (JP); Kenichi Ohba, Tokyo (JP); Masayuki Murata, Tokyo (JP); Fumi Kano, Tokyo (JP); Yoshiyuki Noguchi, Tokyo (JP)

(73) Assignees: NIKON CORPORATION, Tokyo (JP); THE UNIVERSITY OF TOKYO, Tokyo (JP)

( * ) Notice: Subject to any disclaimer, the term of this patent is extended or adjusted under 35 U.S.C. 154(b) by 32 days.

(21) Appl. No.: 16/838,950

(22) Filed: Apr. 2, 2020

(65) Prior Publication Data
US 2021/0073979 A1 Mar. 11, 2021

Related U.S. Application Data

(63) Continuation of application No. PCT/JP2017/036442, filed on Oct. 6, 2017.

(51) Int. Cl.
*G01N 15/10* (2006.01)
*G06T 7/00* (2017.01)
*G01N 15/14* (2006.01)

(52) U.S. Cl.
CPC ....... *G06T 7/0012* (2013.01); *G01N 15/1475* (2013.01); *G06T 2207/30024* (2013.01); *G06T 2207/30242* (2013.01)

(58) Field of Classification Search
CPC ......... G06T 7/0012; G06T 2207/30024; G06T 2207/30242; G01N 15/1475; G01N 2015/1006; G01N 15/1468; G02B 21/365; C12M 1/34
See application file for complete search history.

(56) References Cited

U.S. PATENT DOCUMENTS 9,280,698 B2    3/2016  Kii et al.
2014/0099014 A1*  4/2014  Kii ........................... G06T 7/62
                                                      382/133

OTHER PUBLICATIONS

Dec. 5, 2017 International Search Report issued in International Patent Application No. PCT/JP2017/036442.
Dec. 5, 2017 Written Opinion of the International Searching Authority issued in International Patent Application No. PCT/JP2017/036442.

* cited by examiner

*Primary Examiner* — Siamak Harandi
(74) *Attorney, Agent, or Firm* — Oliff PLC

(57) ABSTRACT

An image-processing device including: a determination unit that determines a captured image on the basis of a ratio of cells and a distribution of the cells in the captured image acquired by imaging a sample including cells; and an area setting unit that sets an area used for analyzing the cells of the sample on the basis of a result of the determination acquired by the determination unit.

15 Claims, 10 Drawing Sheets

IMAGE-PROCESSING DEVICE, IMAGE-PROCESSING METHOD, AND IMAGE-PROCESSING PROGRAM FOR SETTING CELL ANALYSIS AREA BASED ON CAPTURED IMAGE

TECHNICAL FIELD

The present invention relates to an image-processing device, an image-processing method, and an image-processing program.

BACKGROUND ART

In biological science, medical science, and the like, it is known that the states of health, diseases, and the like of organisms, for example, have relations with states of cells, intra-cellular microorganisms, and the like. For this reason, an analysis of such relations becomes one means for solving problems in the biological science, the medical science, and the like. In addition, analyses of transmission paths of information transmitted between cells and inside each cell, for example, can be useful for research on biosensors for industrial use, pharmaceutical use for the purpose of preventing diseases, and the like. As various analysis technologies relating to cells and tissue slices, for example, technologies using image processing are known (for example, see Patent Literature 1).

CITATION LIST

Patent Literature

Patent Literature 1

U.S. Pat. No. 9,280,698

SUMMARY OF INVENTION

According to a first aspect of the present invention, there is provided an image-processing device including: a determination unit that determines a captured image on the basis of a ratio of cells and a distribution of the cells in the captured image acquired by imaging a sample including cells; and an area setting unit that sets an area used for analyzing the cells of the sample on the basis of a result of the determination acquired by the determination unit.

According to a second aspect of the present invention, there is provided an image-processing method including: determining a captured image on the basis of a ratio of cells and a distribution of the cells in the captured image acquired by imaging a sample including cells; and setting an area used for analyzing the cells of the sample on the basis of a result of the determination acquired in the determining of the captured image.

According to a third aspect of the present invention, there is provided an image-processing method program causing a computer to execute: determining a captured image on the basis of a ratio of cells and a distribution of the cells in the captured image acquired by imaging a sample including cells; and setting an area used for analyzing the cells of the sample on the basis of a result of the determination acquired in the determining of the captured image.

Description of Embodiments

Embodiment

Figure 1:
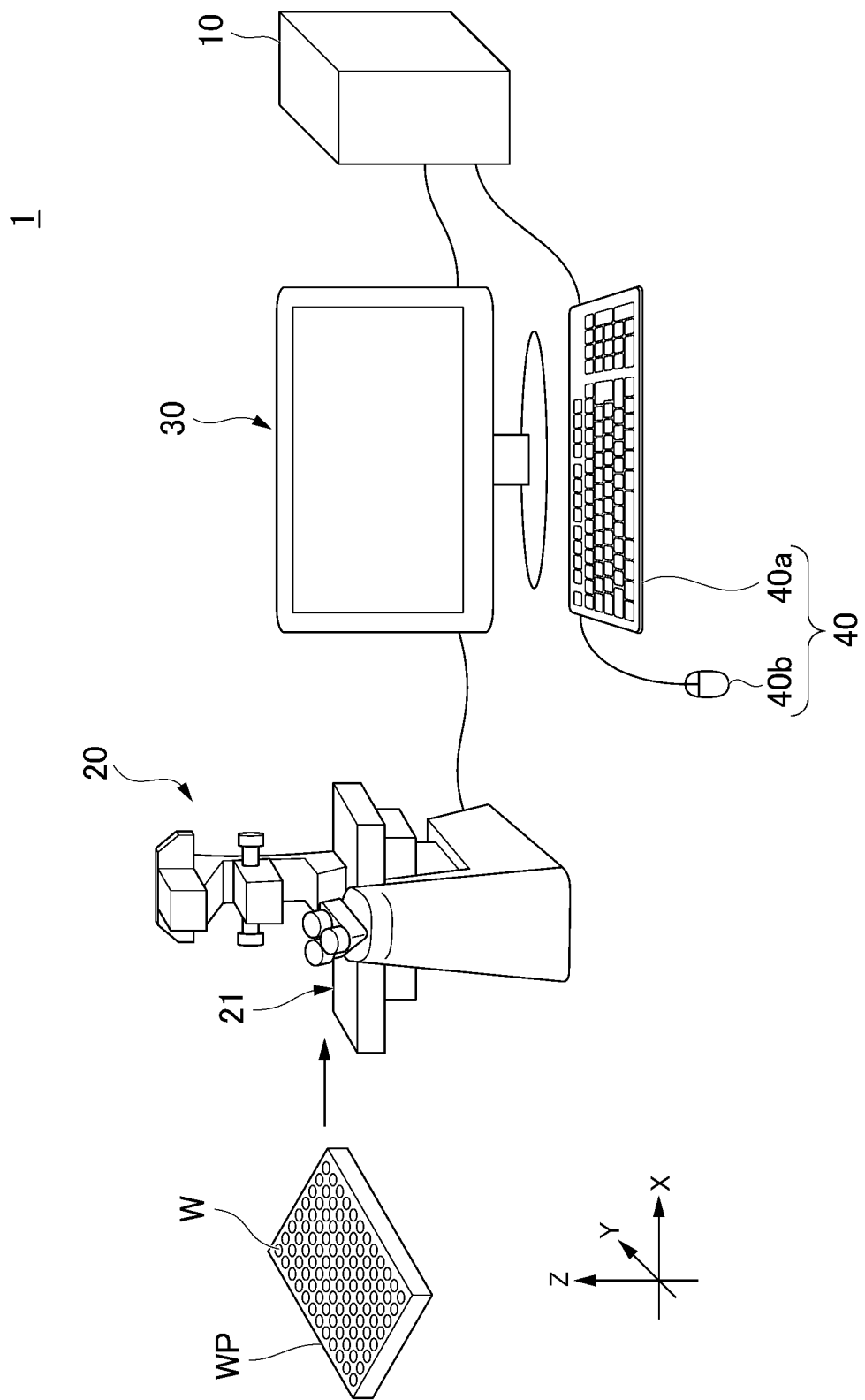
FIG. 1 is a diagram illustrating an example of the configuration of a microscope observation system according to an embodiment of the present invention.

Hereinafter, although an embodiment of the present invention will be described with reference to the drawings, the present invention is not limited thereto. In the following description, an XYZ orthogonal coordinate system will be set, and positional relations between units will be described with reference to the XYZ orthogonal coordinate system. A plane that is orthogonal to an optical axis of an objective lens will be set as an XY plane. A direction parallel to an optical axis of an objective lens will be set as a Z-axis direction. FIG. 1 is a diagram illustrating an example of the configuration of a microscope observation system 1 according to an embodiment of the present invention.

The microscope observation system 1 performs image processing for a captured image acquired by imaging cells and the like.

The microscope observation system 1 includes a microscope device 20, an analysis device 10, a display unit 30, and an operation unit 40.

The microscope device 20 is a microscope that observes an enlarged image of a sample placed on a motor-driven stage 21. More specifically, a sample is a biological sample, a bead, or the like that is an observation target. A biological sample is a fluorescent-dying cell having a thickness or the like. In the following description, an image acquired by imaging a cell or the like will be simply referred to also as a cell image.

A well plate WP is placed on the motor-driven stage 21. The well plate WP includes one to a plurality of wells W. In this embodiment, the well plate WP, as illustrated in FIG. 1, includes 8×12=96 wells W. The number of well plates WP is not limited thereto and may be 4×6=24 wells W, 16×24=384 wells W, 32×48=1,536 wells W, or 64×96=6,144 wells W. A cell is cultured inside a well W under specific experimental conditions. The specific experimental conditions include a temperature, humidity, a culture period, an elapse time after application of a stimulus, a type and an intensity of an applied stimulus, a density, an amount, presence/absence of a stimulus, inducement of biological characteristics, and the like. Here, a stimulus, for example, is a physical stimulus of electricity, a sound wave, magnetism, light, or the like, a chemical stimulus according to administration of a substance or a medicine, or the like. In addition, biological characteristics are characteristics that represent a stage and form of differentiations of cells, the number of cells, a behavior of intra-cell molecules, a form and a behavior of organelles, each shape, behaviors of nuclear bodies, a behavior of DNA molecules, a behavior and a modification of RNA molecules, a behavior and a modification of protein molecules, and the like. In the following description, these biological characteristics will also be described as constituent elements composing a cell. In this example, the microscope device 20 observes sown cells in each of the plurality of wells W included in the well plate WP.

The analysis device 10 is a computer device that analyzes a captured image captured by the microscope device 20. In this example, the analysis device 10 selects a field of vision of a captured image that is appropriate for an analysis on the basis of a pre-captured image captured by the microscope device 20. Here, the pre-captured image is a captured image that is used for selecting a field of vision of a captured image that is appropriate for an analysis. The pre-captured image, for example, is an image of which a pixel size is larger than that of a main captured image or an image that has been captured with a magnification lower than the capture magnification of the main captured image. The main captured image is a captured image that is used for an analysis of cells. Here, the field of vision is a position to be captured on the XY plane in the Z-axis direction in a well W described above. In this example, the position to be captured is a certain face of the XY plane at a certain position in the Z-axis direction. In this embodiment, the Z-axis direction is a thickness direction of a cell.

The analysis device 10 analyzes a cell imaged in the main captured image captured in the selected field of vision.

The display unit 30, for example, includes a liquid crystal display and displays images such as a captured image analyzed by the analysis device 10 and the like. In the images displayed on this display unit 30, an image generated on the basis of a result of an analysis performed by the analysis device 10 is included.

The operation unit 40 is operated by a user. When the operation unit 40 is operated by a user, the operation unit 40 outputs an operation signal. This operation signal is supplied to the analysis device 10. The analysis device 10 acquires various kinds of information supplied from a user on the basis of operation signals supplied from the operation unit 40. As examples of the operation unit 40, there are a keyboard 40a, a mouse 40b, and the like.

Next, an example of the functional configuration of the microscope observation system 1 will be described with reference to FIG. 2.

Figure 2:
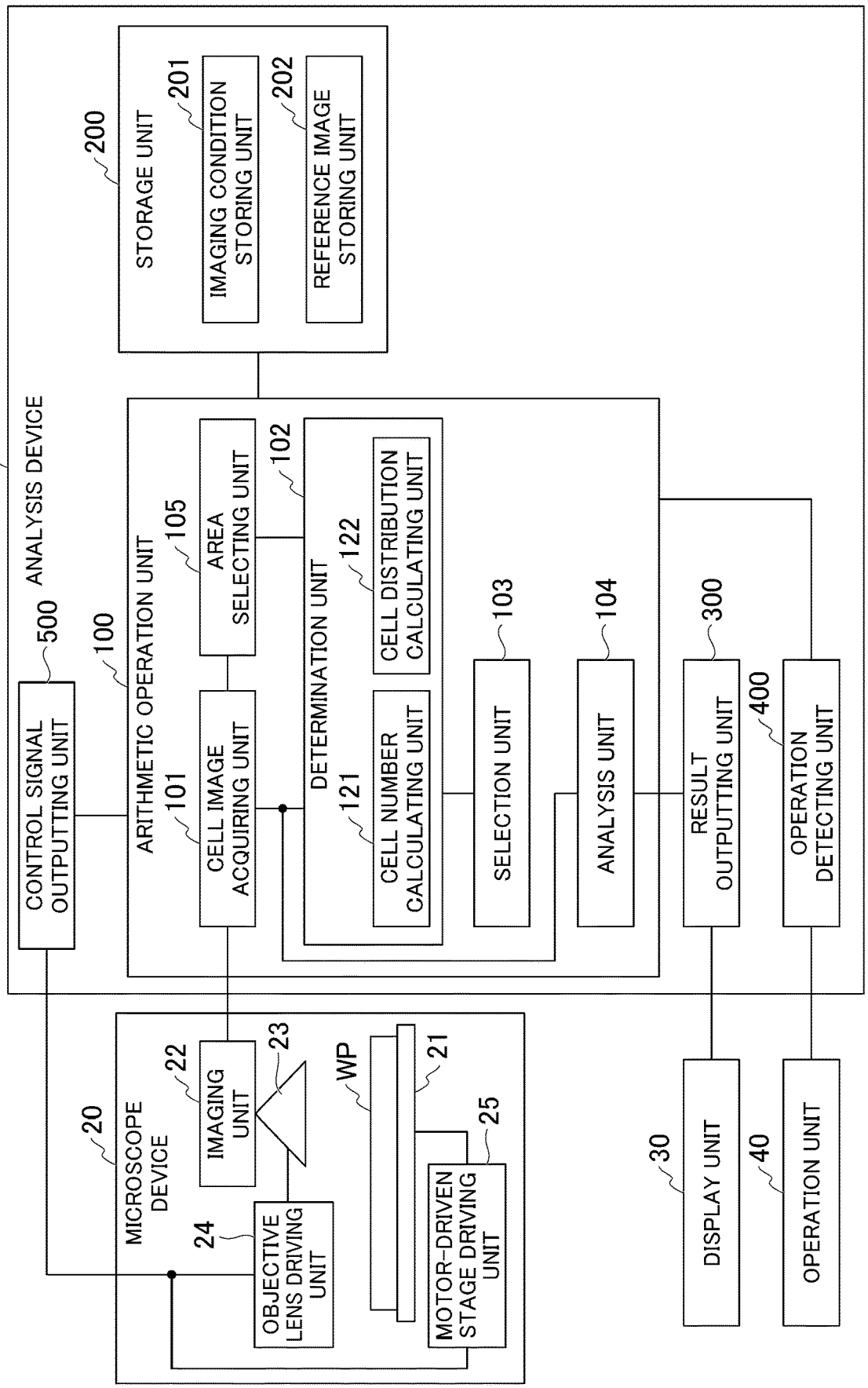
FIG. 2 is a block diagram illustrating an example of the functional configuration of a microscope observation system.

FIG. 2 is a block diagram illustrating an example of the functional configuration of the microscope observation system 1.

The microscope device 20 is a biological microscope and includes a motor-driven stage driving unit 25, an imaging unit 22, an objective lens 23, and an objective lens driving unit 24 in addition to the motor-driven stage 21 described above.

The motor-driven stage 21 can arbitrarily operate the position of an imaging target object in a predetermined direction (for example, a certain direction in a two-dimensional plane disposed in the horizontal direction). The motor-driven stage 21 is driven by the motor-driven stage driving unit 25. The motor-driven stage driving unit 25 includes a motor that operates the position of the motor-driven stage 21 in an X-axis direction or a Y-axis direction that are directions orthogonal to an optical axis of the objective lens 23. By driving the motor, the motor-driven stage driving unit 25 can operate the motor-driven stage 21 in the X-axis direction or the Y-axis direction. The microscope device 20 may not include the motor-driven stage 21, and the stage may be a stage that is not operated in a predetermined direction. In such a case, a user operating the microscope device 20 may move the well plate WP placed on the motor-driven stage 21 and supply the position of the well plate WP after the movement from the operation unit 40 to the analysis device 10.

The imaging unit 22 includes an imaging device such as a charge-coupled device (CCD), a complementary MOS (CMOS), or the like and images an imaging target disposed on the motor-driven stage 21. An image of cells placed on the motor-driven stage 21 is formed on an imaging face of the imaging unit 22 through the objective lens 23 in accordance with an imaging lens not illustrated in the drawing.

The objective lens 23 receives light that has been transmitted through a cell. Light that is received by the objective lens 23 is not limited to the light that has been transmitted through a cell. The objective lens 23 may receive light that has been reflected by a cell. The objective lens 23, for example, may be an immersion objective lens such as an oil-immersion objective lens or a water-immersion objective lens or may be a dry objective lens not corresponding to immersion.

The objective lens driving unit 24 includes a motor that operates the position of the objective lens 23 in the Z-axis direction that is an optical axis direction and can operate the objective lens 23 in the Z-axis direction by vertically moving a revolver, which is not illustrated, holding the objective lens 23.

More specifically, the microscope device 20, for example, has the functions of a differential interference contrast microscope (DIC), a phase-contrast microscope, a fluorescence microscope, a confocal microscope, a super-resolution microscope, a two-photon excitation fluorescence microscope, a light-sheet microscope, a light-field microscope, a quantification phase-contrast microscope, a holographic microscope, and the like.

The microscope device 20 images a culture vessel placed on the motor-driven stage 21. This culture vessel, for example, is a well plate WP, a slide chamber, or the like. The microscope device 20 images transmission light that has been transmitted through cells as an image of the cells by emitting light onto the cells cultured inside a plurality of wells W included in the well plate WP. In accordance with this, the microscope device 20 can acquire an image such as a transmissive DIC image, a phase-contrast image, a dark field image, a bright field image, or the like of cells.

In addition, by emitting excitation light exciting a fluorescent material to cells, the microscope device 20 images fluorescence emitted from biological materials as an image of the cells.

In this embodiment, a cell image is acquired by causing fluorescence fused proteins to be expressed, dying a cell in a living state using a chemical reagent or the like, and the like. In another embodiment, a cell image is acquired by fixing and dying cells. Fixed cells stop metabolism. Thus, in a case in which, after a stimulus is applied to a cell and changes inside the cell with respect to time are observed using the fixed cell, a plurality of cell culture vessels in which the cell is cultured need to be prepared. For example, there are cases in which a stimulus is applied to a cell, and a change in the cell after a first time and a change in the cell after a second time different from the first time are desired to be observed. In such cases, a stimulus is applied to the cell, and, after the first time elapses, the cell is fixed and dyed, and a cell image is acquired.

A culture vessel of a cell different from the cell used for the observation at the first time is prepared, a stimulus is applied to the cell, and, after the second time elapses, the cell is fixed and dyed, and a cell image is acquired. In this way, by observing a change in the cell at the first time and a change in the cell at the second time, changes inside the cell with respect to time can be estimated. The number of cells used for observing changes inside the cells at the first time and the second time is not limited to one. Thus, images of a plurality of cells are acquired at the first time and the second time, respectively. For example, in a case in which the number of cells for which changes inside the cells are to be observed is 1000, 2000 cells are imaged at the first time and the second time. Thus, in a case in which details of changes inside cells for a stimulus are to be acquired, a plurality of cell images are required for each timing for imaging from the stimulus, a large quantity of cell images are acquired.

The microscope device 20 may image emitted light or fluorescence from a coloring substance taken into a biological material or emitted light or fluorescence generated in accordance with a substance having chromophore being combined with a biological material as an image of cells described above. In accordance with this, the microscope observation system 1 can acquire a fluorescence image, a confocal image, a super-resolution image, a two-photon excitation fluorescence microscope image.

The method of acquiring an image of cells is not limited to that using an optical microscope. For example, the method of acquiring an image of cells may be that using an electronic microscope. In other words, the type of images of cells may be appropriately selected.

In this embodiment, cells, for example, are first stage culture cells, established culture cells, cells of a tissue section, and the like. As a sample to be observed for observing cells, an aggregated body of cells, a tissue sample, an organ, or an individual (an animal or the like) may be used for observation, and an image including the cells may be acquired. The state of cells is not particularly limited and may be either a living state or a fixed state. It is apparent that information of a living state and information of a fixed state may be combined.

In addition, cells may be processed using chemical light emission or fluorescent proteins (for example, chemical light emission or fluorescent proteins expressed from a transduced gene (a green fluorescent protein (GFP) or the like)) and be observed. Alternatively, cells may be observed using immunostaining or dying using a chemical reagent. Furthermore, they may be combined for observation. For example, a light emission protein to be used may be selected in accordance with a type of intracellular structures (for example, organelles (cell organelles) such as a Golgi body and the like) to be determined.

In addition, a means for observing such cells and preprocessing for an analysis such as a method of dying cells and the like may be appropriately selected in accordance with the purpose. For example, in a case in which dynamic behaviors of cells are to be acquired, dynamic information of the cells may be acquired using an optimal technique, and, in a case in which intracellular signal transduction is to be acquired, information relating to the intracellular signal transduction may be acquired using an optimal technique. There may be a difference in preprocessing to be selected in accordance with the purpose.

The analysis device 10 is an analysis device that analyzes cells. For example, the analysis device 10 analyzes a response of cells for a stimulus. In this embodiment, the analysis device 10 is a computer device that selects a field of vision imaged in a captured image used for an analysis and analyzes cells imaged in the captured image in which cells are imaged in an appropriate field of vision that is appropriate for the analysis.

The analysis device 10 includes an arithmetic operation unit 100, a storage unit 200, a result outputting unit 300, an operation detecting unit 400, and a control signal outputting unit 500.

The arithmetic operation unit 100 functions in accordance with a processor executing a program stored in the storage unit 200. Some or all of functional units of such an arithmetic operation unit 100 may be configured by hardware such as Large Scale Integration (LSI) or an Application Specific Integrated Circuit (ASIC). The arithmetic operation unit 100 includes a cell image acquiring unit 101, a determination unit 102, an area selecting unit 105, a selection unit 103, and an analysis unit 104 as functional units thereof. The determination unit 102 includes a cell number calculating unit 121 and a cell distribution calculating unit 122.

The cell image acquiring unit 101 acquires a cell image from another device that captures a captured image. In this example, the cell image acquiring unit 101 acquires a cell image captured by the imaging unit 22 included in the microscope device 20 and supplies the acquired cell image to the area selecting unit 105, the determination unit 102, and the analysis unit 104. In the following description, a cell image acquired by the cell image acquiring unit 101 will be also referred to as an observation image.

Here, in observation images acquired by the cell image acquiring unit 101, a plurality of images in which culture states of cells are imaged in a time series and a plurality of images in which cells are cultured under various experimental conditions are included.

The determination unit 102 determines a cell image on the basis of the number of cells imaged in a cell image in which the cells are imaged in different fields of vision and a distribution of the cells. In this embodiment, the determination unit 102 calculates the number of cells and a distribution of the cells on the basis of an image of cell nucleuses included in the cells imaged in the cell image. In other words, the determination unit 102 determines whether or not cells are imaged on the basis of luminance of fluorescence from cell nucleuses. In addition, the determination unit 102 calculates the number of cells and a distribution of the cells on the basis of a pre-captured image that is an image of which resolution is lower than that of the main captured image used for an analysis. In accordance with this, the determination unit 102 can perform determination in a shorter time than that in a case in which the number of cells and a distribution of the cells are calculated on the basis of the main captured image. An image used by the determination unit 102 for calculating the number of cells and the distribution of the cells is not limited to the pre-captured image of which resolution is lower than that of the main captured image. The resolution of the main captured image and the resolution of the pre-captured image may be different from each other or be the same. In addition, the resolution of the pre-captured image may be higher than the resolution of the main captured image. Here, the resolution, for example, is a value that represents a density of pixels in an image. In a case in which an image having low resolution and an image having high resolution are compared with each other, the fineness of lattices representing an image differs. For example, in a case in which the number of lattices per inch is represented as a number, the image having low resolution has a small number.

The pre-captured image and the main captured image are not limited to images that are captured at different times. For example, a high-resolution image is captured, thereafter, a low-resolution image is generated, and an area is set in the low-resolution image, and a high-resolution image corresponding to the set area may be used for an analysis. In other words, an image used for calculating the number of cells and a distribution of the cells and an image used for an analysis may be the same. Thus, there may be no pre-captured image. It is apparent that the resolution of the pre-captured image and the resolution of the main captured image may be the same.

In addition, the number of cells and a distribution of the cells calculated from the pre-captured image and the number of cells and a distribution of the cells calculated through an analysis of the main captured image may be different from each other. For example, there are cases in which, the pre-captured image and the main captured image have different resolutions, and, for example, the number of cells is calculated as 100 from the pre-cell image, an analysis is performed for a set area, and the number of cells is calculated as 110 for the set area. In such cases, there may be a difference of an allowed degree between a result of calculation of the pre-cell image and a result of calculation of the main captured image. For example, a difference between a result of calculation of the pre-cell image and a result of calculation of the main captured image may be 10%, 20%, 30%, 40%, 50%, 60%, 70%, 80%, 90%, 100%, or more. In addition, in a case in which there is a large difference between a result of calculation of the pre-cell image and a result of calculation of the main captured image, and an analysis cannot be performed with the number of cells and the ratio of the cells, which are desired being set, the resolution of the pre-captured image may be changed.

More specifically, the determination unit 102 calculates the number of cells imaged in an observation image using the cell number calculating unit 121. The determination unit 102 calculates a distribution of cells imaged in an observation image using the cell distribution calculating unit 122. The determination unit 102 can determine whether or not the number of cells calculated by the cell number calculating unit 121 and the distribution of the cells calculated by the cell distribution calculating unit 122 satisfy a predetermined number of cells and a predetermined distribution of the cells being used for analyzing the cells. Here, the predetermined number, for example, may be the number of cells that is 10, 20, 30, or 40 or more, and, for example, the predetermined number may be satisfied in a case in which the number of cells is within a predetermined range such as the number of cells being in the range of 10 to 20. In addition, the number of cells may have any other numerical value or be in the range of other numerical values. The determination unit 102 determines whether or not an observation image used for determination is appropriate for an analysis by comparing the number of cells calculated by the cell number calculating unit 121 with the number of cells determined in advance by a user. Similarly, the determination unit 102 determines whether or not an observation image used for determination is appropriate for an analysis by comparing the distribution of cells calculated by the cell distribution calculating unit 122 with the distribution of cells determined in advance by a user. The determination unit 102 determines whether or not an observation image used for determination is appropriate for an analysis on the basis of a result of determination for the observation image that is acquired by the cell number calculating unit 121 and a result of determination for the observation image that is acquired by the cell distribution calculating unit 122.

In this embodiment, the cell number calculating unit 121 calculates the number of cells images in the pre-captured image by calculating the number of cell nucleuses. In addition, the cell distribution calculating unit 122 calculates the distribution of cells imaged in the pre-captured image by calculating a distribution of cell nucleuses.

In addition, the predetermined number of cells and the predetermined distribution of cells differ in accordance with the type of cells sown into the well plate WP and analysis details. In the following description, the predetermined number of cells and the predetermined distribution of cells are also referred to as imaging conditions for selecting an imaging area for capturing an analysis image. In the imaging conditions, an area of cells in the observation image may be included in addition to the number of cells and the distribution of the cells in the observation image. In addition, the imaging conditions may be a type of cells in the observation image. The type of cells, for example, may be a degree of canceration of the cells, and the imaging conditions may be an occupancy ratio of cancerated cells in the observation image. In addition, the imaging conditions may be rephrased as selection conditions for selecting an imaging position that is used for capturing an analysis image. These imaging conditions are stored in an imaging condition storing unit 201. A user may select an arbitrary imaging condition from the imaging conditions stored in the imaging condition storing unit 201. In addition, a user may supply this imaging condition to the analysis device 10 by operating the operation unit 40.

In order to select an imaging position, the number of cells and the distribution of the cells in the observation image are stored as conditions. For example, in the case of the number of cells, although the number of cells is stored as a numerical value equal to or larger than 100, the number of cells is not limited thereto. For example, by performing comparison with an image having a target number of cells and a target distribution of cells as a reference image, an imaging position appropriate for an analysis may be determined. In the following description, a captured image representing imaging conditions may be also referred to as a reference image. In this case, the reference image is stored in a reference image storing unit 202. The determination unit 102 determines a cell image acquired by the cell image acquiring unit 101 on the basis of the reference image.

The area selecting unit 105 selects an area used for pre-capturing on the XY plane of the well W. In this embodiment, an area used for pre-capturing will be referred to as a pre-imaging area. The pre-imaging area is a candidate for an area that is mainly captured. The area selecting unit 105 acquires a low-magnification image that is a captured image captured with magnification lower than an analysis image magnification from the cell image acquiring unit 101. In this example, the low-magnification image is an image in which a schematically complete view of the well W is imaged. The analysis image magnification is a magnification at which an image used for analyzing cells is captured. In this embodiment, the low-magnification image is an image that is captured with a magnification lower than the pre-capturing magnification from the cell image acquiring unit 101. The pre-capturing magnification is a magnification with which a pre-capturing image is captured.

The area selecting unit 105 selects an imaging position of the pre-imaging area on the basis of a result of determination acquired by the determination unit 102 using the low-magnification image acquired from the cell image acquiring unit 101. The determination unit 102, for example, uses an image in which part of the low-magnification image supplied from the area selecting unit 105 is included and calculates whether or not an area included in this image is appropriate as a pre-imaging area used for pre-capturing. Thus, the determination unit 102 determines the number of cells and a distribution of the cells. In this case, conditions used for determination performed by the determination unit 102 may be the same as or different from imaging conditions used for an analysis to be described below. For example, in a case in which an area in which part of a cell is not imaged is present in the low-magnification image, a position of an area in which cells are included is determined by the determination unit 102, and a result thereof may be supplied to the area selecting unit 105. In other words, presence/absence of a cell may be set as conditions for selecting an imaging position of a pre-captured image. The determination unit 102 determines the number of cells and a distribution of the cells for every position to which an imaging position with an imaging magnification is changed on the XY plane at the time of performing pre-capturing using the low-magnification image supplied from the area selecting unit 105, compares a result thereof with the number of cells and the distribution of cells determined in advance by a user, and supplies whether the number of cells and the distribution of cells determined in advance by the user are satisfied to the area selecting unit 105 together with information representing the imaging position. The area selecting unit 105 that has received the supplied information selects an imaging position satisfying the number of cells and the distribution of cells determined in advance by the user as a pre-imaging area for pre-capturing.

More specifically, the area selecting unit 105 cuts out an image in an imaging range corresponding to the magnification used for pre-capturing from the low-magnification image acquired from the cell image acquiring unit 101 and supplies the image to the determination unit 102. In the following description, this cut-out image will be also referred to as a cut image. In other words, the cut image is an image in which a field of vision of the same range as that of the pre-captured image on the XY plane is imaged. The determination unit 102 acquires a cut image from the area selecting unit 105. The determination unit 102 determines whether or not the range cut in the cut image is appropriate for an imaging range for capturing a pre-captured image on the basis of the cut image acquired from the area selecting unit 105. In other words, the determination unit 102 determines whether or not a position cut out in the cut image is appropriate for an imaging position at which a pre-captured image is captured on the basis of the cut image acquired from the area selecting unit 105. In a case in which there are a plurality of imaging positions that are appropriate for a pre-captured image, a plurality of pre-captured images may be captured. An imaging position coinciding more with conditions for pre-capturing set by the user may be selected from among the plurality of imaging positions that are appropriate for a pre-captured image, and a pre-captured image may be captured at the selected imaging position. Only one imaging position that is appropriate for a pre-captured image may be selected. The determination unit 102 supplies a result of the determination to the area selecting unit 105. The area selecting unit 105 acquires the result of the determination of the cut image from the determination unit 102. A cut area of the cut image on the XY plane may be the same as or different from the imaging area of the pre-captured image.

In a case in which the result of the determination acquired from the determination unit 102 indicates that the conditions determined in advance by the user are satisfied, the area selecting unit 105 outputs a signal for pre-capturing an area in which the cut image is captured from the control signal outputting unit 500 to the microscope device 20. The microscope device 20 pre-captures the area, in which the cut image is captured, selected by the area selecting unit 105 with a high magnification on the basis of a control signal acquired from the control signal outputting unit 500.

In a case in which the result of the determination acquired from the determination unit 102 indicates that the conditions determined in advance by the user are not satisfied, the area selecting unit 105 supplies a cut image for which an imaging position at which the pre-captured image is captured has been changed to the determination unit 102.

The determination unit 102 acquires a pre-captured image from the cell image acquiring unit 101. The selection unit 103 acquires a result of determination for each pre-captured image from the determination unit 102. The selection unit 103 selects an imaging position at which a main captured image that is a captured image used for analyzing cells on the basis of the result of determination for each pre-captured image acquired from the determination unit 102 is captured. In this embodiment, the selection unit 103 selects an imaging position for main capturing on the basis of the result of determination of imaging conditions acquired from the determination unit 102. In addition, in this case, information of the imaging area of the captured image determined by the determination unit 102 is transmitted together to the selection unit 103. In accordance with this, the selection unit 103 can select an imaging area to be mainly captured. In other words, the selection unit 103 can set an imaging area to be used for an analysis. In accordance with this, the captured image in the imaging area set by the selection unit 103 becomes an image satisfying imaging conditions for an analysis. Thus, the selection unit 103 can set an imaging area satisfying the imaging conditions for an analysis in the wells. In a case in which there are a plurality of imaging areas satisfying the imaging conditions set in advance by the user on the basis of the result of determination of the imaging conditions acquired from the determination unit 102, all the imaging areas that become a plurality of candidates may be set as captured images for an analysis, or an imaging area used for an analysis may be further selected from the imaging areas that become the plurality of candidates. In a case in which an imaging area is selected from the plurality of candidates, the plurality of candidates may be further compared with the imaging conditions, and an imaging area that is more optimal may be selected. For example, in a case in which the number of cells as the imaging conditions is in the range of 100 to 500, when a value close to 300 is preferable as the number of cells as the imaging conditions, a candidate of which the number of cells is close to 300 may be selected from among the plurality of candidates.

The selection unit 103 outputs a signal used for capturing a main captured image with the field of vision selected as a field of vision for main capturing from the control signal outputting unit 500 to the microscope device 20. The microscope device 20 mainly captures the field of vision selected by the selection unit 103 on the basis of a control signal acquired from the control signal outputting unit 500. The imaging area at the time of pre-capturing may be the same as or different from the imaging area at the time of main capturing.

The analysis unit 104 acquires a main captured image from the cell image acquiring unit 101. The analysis unit 104 analyzes cells imaged in the main captured image acquired from the cell image acquiring unit 101. Here, the analyzing, for example, is to analyze a correlation of cells imaged in the main captured image. This correlation is calculated from feature quantities of the cells imaged in the main captured image. In these feature quantities, luminance of a cell image, a cell area inside the image, a dispersion of luminance of cell images inside the image, a form, and the like are included. In other words, the feature quantities are features derived from information acquired from a cell image to be captured. For example, the analysis unit 104 calculates a luminance distribution in the main captured image acquired from the cell image acquiring unit 101. The analysis unit 104 may use a plurality of different images in a time series or according to changes in the cell state such as differentiation, acquire position information representing a change in the luminance that is different from the others from a change in the calculated luminance distribution in a predetermined time or a change in the calculated luminance distribution accompanying a cell state change such as differentiation, and set the change in the luminance as a feature quantity.

The analysis unit 104 analyzes cells imaged in the main captured image by performing a multi-scale analysis of the calculated feature quantity. The multi-scale analysis, for example, is performed using a graphical Lasso method or the like. In this embodiment, the graphical Lasso method is an efficient algorithm for estimating an accuracy matrix from an L1 regularized Gaussian model. For example, it has been described in "Sparse inverse covariance estimation with the graphical lasso", written by Jerome Friedman, Trevor Hastie, and Robert Tibshirani, Biostatistics (2008), 9,3 432-441.

The analysis unit 104 supplies a result of the analysis to the result outputting unit 300.

The result outputting unit 300 acquires the result of the analysis from the analysis unit 104. The result outputting unit 300 causes the display unit 30 to display the result of the analysis acquired from the analysis unit 104.

Overview of Operation of Analysis Device

Next, a specific calculation process of the analysis device 10 will be described with reference to FIGS. 3 to 9.

Overview of Operation of Area Selecting Unit

A specific calculation process of the area selecting unit 105 selecting an imaging position at which a pre-captured image is captured will be described with reference to FIG. 3.

Figure 3:
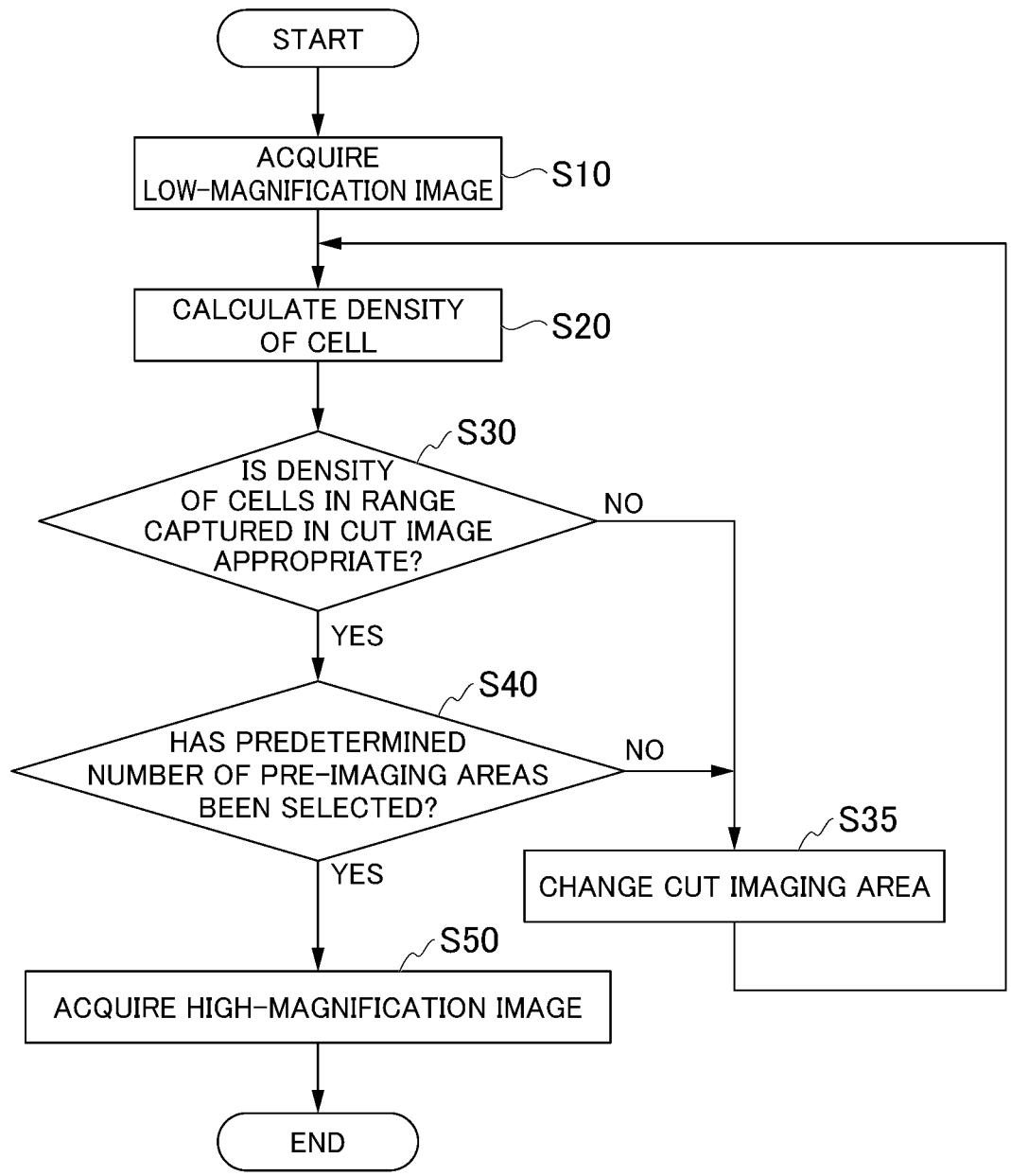
FIG. 3 is a flowchart illustrating an example of an operation process of an area selecting unit according to this embodiment.

FIG. 3 is a flowchart illustrating an example of an operation process of the area selecting unit 105 according to this embodiment. The operation process illustrated here is an example, and an operation sequence may be omitted, or an operation sequence may be added.

The area selecting unit 105 acquires a low-magnification image from the cell image acquiring unit 101 (Step S10).

Here, an example of an imaging position at which a low-magnification image selected by the area selecting unit 105 and a pre-captured image is captured will be described with reference to FIG. 4.

Figure 4:
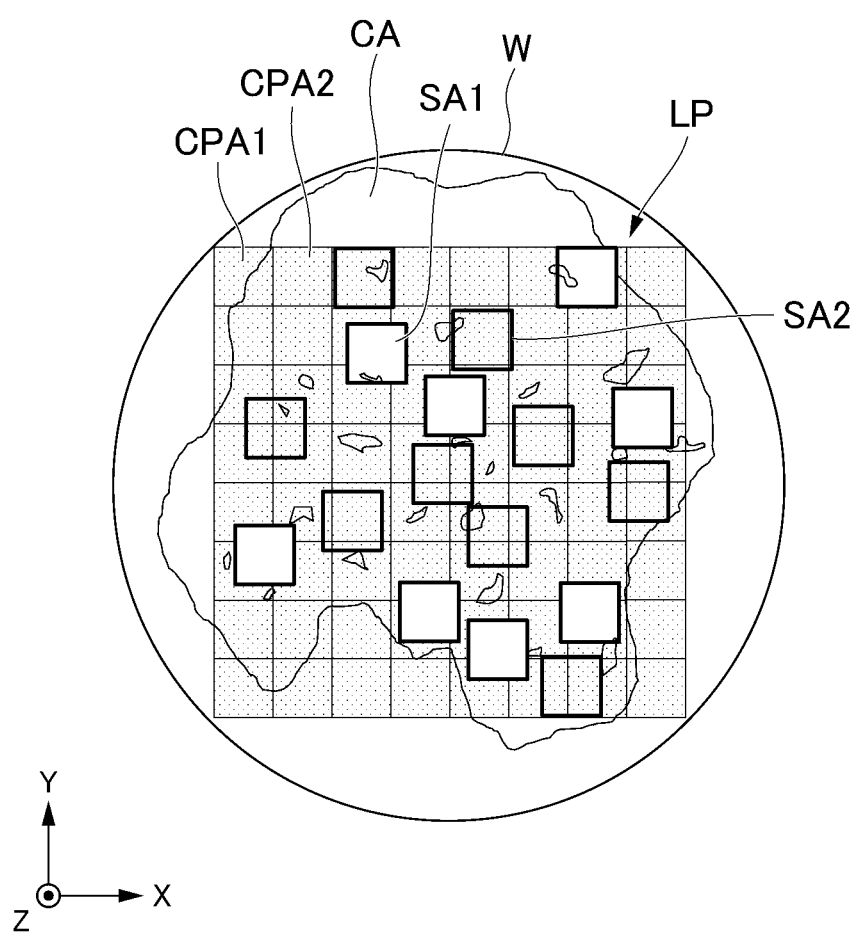
FIG. 4 is a diagram illustrating an example of a low-magnification image and a pre-imaging area.

FIG. 4 is a diagram illustrating an example of an imaging position at which a low-magnification image and a pre-captured image are captured.

The area selecting unit 105 acquires a low-magnification image LP from the cell image acquiring unit 101. As described above, in this example, the low-magnification image LP is an image in which a schematically complete view of the well W is imaged. In the well W, there is a sowing area CA that is an area in which cells are sown. In this sowing area CA, cells cannot be uniformly sown in accordance with various conditions. In the sowing area CA, for example, there are cells after culture, and thus, a direction in which the number of cells increases according to culture is not constant in a culture period, and, for example, there are cases in which the cells are cultured in a specific direction, and therefore, the cell may not be uniformly distributed. For this reason, in the sowing area CA, there are an area in which the number of cells is small, and an area that is not appropriate for an analysis due to overlapping between cells are included. For this reason, the area selecting unit 105 selects an area that is appropriate for an analysis from the sowing area CA as a pre-imaging area.

Referring back to FIG. 3, the area selecting unit 105 calculates a density of the cells (Step S20). More specifically, the area selecting unit 105 generates cut images from the low-magnification image LP acquired from the cell image acquiring unit 101. In this example, the cut images, for example, as illustrated in FIG. 4, are images acquired by cutting out areas such as a cut image area CPA1 and a cut image area CPA2 from the low-magnification image LP. In the following description, when the cut image area CPA1 and the cut image area CPA2 do not need to be identified from each other, they will be simply referred to as cut image areas CPA. In this example, the cut image areas CPA are areas acquired by equally dividing horizontal and vertical lengths of the low-magnification image LP into respective eight parts. The size of each of eight equally-divided areas is an imaging range in a case in which imaging is performed with the analysis image magnification described above. The cut image areas CPA are not limited to these eight equally-divided areas. In other words, the cut image areas CPA may be set as certain areas in the sowing area CA.

The area selecting unit 105 supplies the cut images to the determination unit 102. The determination unit 102 acquires the cut images from the area selecting unit 105. The determination unit 102 calculates a density of the cells on the basis of the cut images acquired from the area selecting unit 105. Here, a density of cells is the number of the cells or a distribution of the cells described above. In addition, the determination unit 102 may calculate a degree of overlapping between cells as a density of the cells. In a case in which the amount of overlapping between cells imaged in a cell image becomes smaller, the cell image is an image that is more appropriate for an analysis. The determination unit 102 determines whether or not a field of vision imaged in the cut image is a field of vision that is appropriate for pre-capturing on the basis of the calculated density of the cells. The determination unit 102 determines whether or not an area imaged in the cut image is an area that is appropriate for pre-capturing on the basis of the calculated density of the cells. The determination unit 102 supplies a result of the determination to the area selecting unit 105.

The area selecting unit 105 acquires the result of determination from the determination unit 102. The area selecting unit 105 determines whether or not a field of vision imaged in the cut image is appropriate as a field of vision in which a pre-captured image is captured on the basis of the result of determination acquired from the determination unit 102 (Step S30).

In a case in which the result of the determination acquired from the determination unit 102 indicates that a field of vision that is appropriate for pre-capturing has not been imaged (No in Step S30), the area selecting unit 105 generates cut images acquired by changing the cut image areas CPA (Step S35). More specifically, the area selecting unit 105 generates cut images of which cutting areas are different in the direction of the XY plane from the low-magnification image LP. The area selecting unit 105 repeats the processes of Steps S20 to S30.

In addition, in a case in which a pre-imaging area has already been selected, the area selecting unit 105 selects areas in which an area not overlapping the pre-imaging area that has been selected has been imaged as cut image areas CPA. Therefore, the area selecting unit 105 can select a plurality of areas as candidates for a pre-imaging area. Each of the selected candidate areas for the pre-imaging area is a different area inside a well, and thus, cells included in the imaging area are different. Thus, since the number of cells included in the candidate areas for the pre-imaging area and a distribution of the cells, and the like are different, the possibility of selecting an image coinciding with conditions such as the number of cells, a distribution of the cells, and the like required for the pre-imaging area determined in advance can be raised. Thus, since a plurality of places can be selected as pre-imaging areas, the determination unit 102 can determine whether the plurality of pre-imaging areas are appropriate for the imaging conditions.

In a case in which the result of the determination acquired from the determination unit 102 indicates that a field of vision that is appropriate for pre-capturing is imaged, the area selecting unit 105 determines that a predetermined number of pre-imaging areas have been selected (Step S40). This predetermined number may be stored in the imaging condition storing unit 201 in advance or may be a number designated by a user. For example, the area selecting unit 105 selects areas such as a pre-imaging area SA1, a pre-imaging area SA2, and the like illustrated in FIG. 4.

In a case in which it is determined that a predetermined number of pre-imaging areas have not been selected (No in Step S40), the area selecting unit 105 executes the process of Step S35 described above.

In a case in which it is determined that a predetermined number of pre-imaging areas have been selected (Yes in Step S40), the area selecting unit 105 causes the microscope device 20 to perform pre-capturing of the selected pre-imaging areas with a high magnification. The cell image acquiring unit 101 acquires a pre-capturing image that is a high magnification image from the imaging unit 22 (Step S50).

Here, an example of pre-imaging areas selected by the area selecting unit 105 will be described with reference to FIG. 5.

Figure 5:
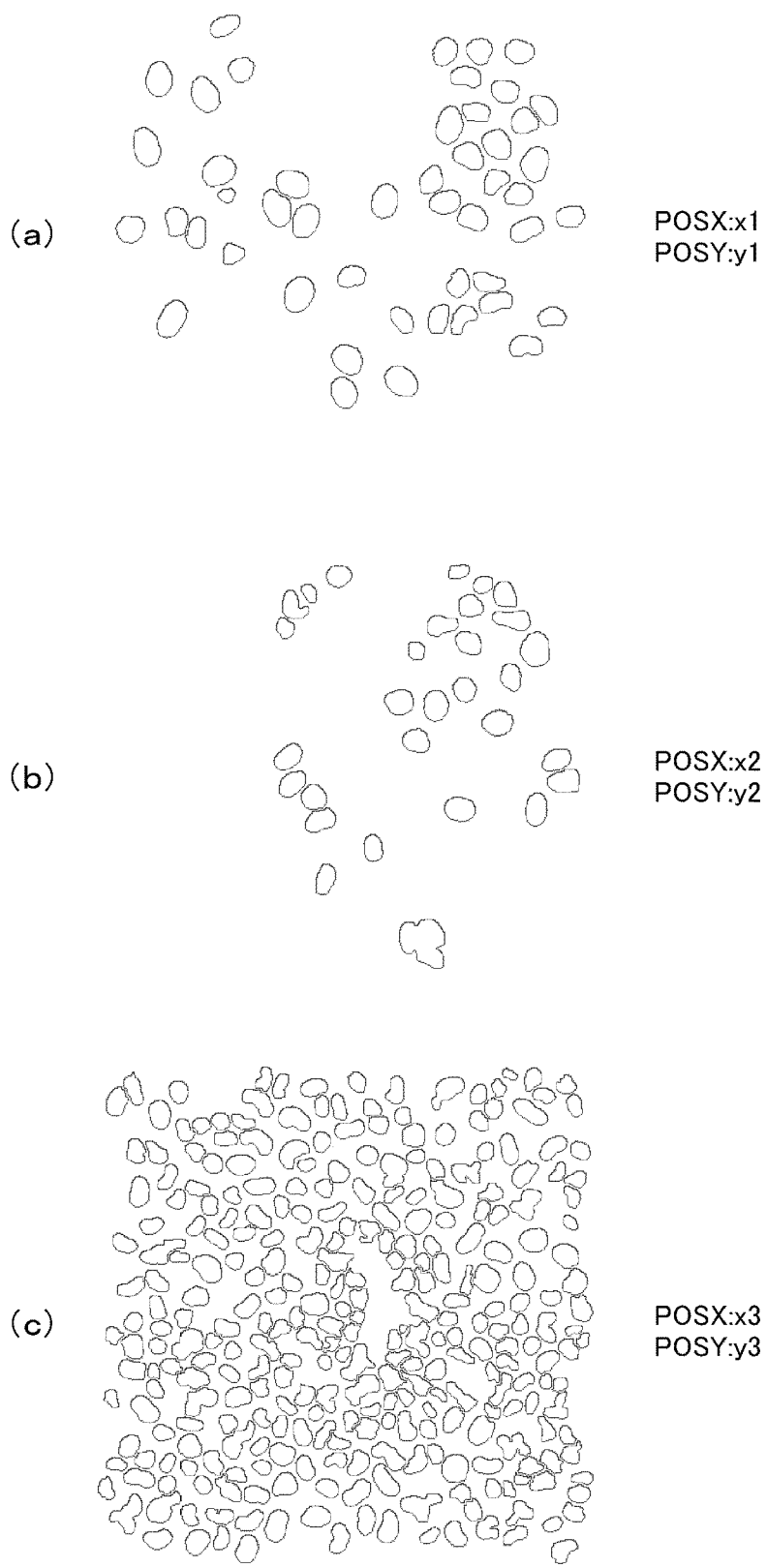
FIG. 5 is a diagram illustrating an example of a cut-out image.

FIG. 5 is a diagram illustrating an example of cut images.

FIG. 5(*a*) is a cut image in which an X-axis position POSX: x1 and a Y-axis position POSY: y1, which represents an area satisfying imaging conditions, is imaged. The cut image illustrated in FIG. 5(*a*) is an image in which an area of which a density of cells is appropriate has been imaged. In other words, the cut image illustrated in FIG. 5(*a*) is an image in which a field of vision in which the number of cells and a distribution of the cells satisfy imaging conditions has been captured. The position POSX: x1 and the position POSY: y1 are selected as a pre-imaging area.

FIG. 5(*b*) is a cut image in which an X-axis position POSX: x2 and a Y-axis position POSY: y2, which represents an area not satisfying the imaging conditions, is imaged. The cut image illustrated in FIG. 5(*b*) is an example of a case in which the number of cells that have been imaged and a distribution of the cells do not satisfy the imaging conditions. In other words, the cut image illustrated in FIG. 5(*b*) is an image in which a field of vision in which the number of cells and a distribution of the cells do not satisfy the imaging conditions has been captured. The position POSX: x2 and the position POSY: y2 are not selected as a pre-imaging area.

FIG. 5(*c*) is a cut image in which an X-axis position POSX: x3 and a Y-axis position POSY: y3, which represents an area not satisfying the imaging conditions, is imaged. The cut image illustrated in FIG. 5(*c*) is an example of a case in which the imaging conditions are not satisfied. The cells imaged in the cut image illustrated in FIG. 5(*c*) have bad extension due to coagulation of the cells. In other words, the number of cells included in the cut image illustrated in FIG. 5(*c*) is larger than the number of cells represented in the imaging conditions. The position POSX: x3 and the position POSY: y3 are not selected as a pre-imaging area.

Overview of Operation of Main Capturing

Next, a specific operation process until a pre-imaging area selected by the area selecting unit 105 is mainly captured in Step S50 described above will be described with reference to FIG. 6.

Figure 6:
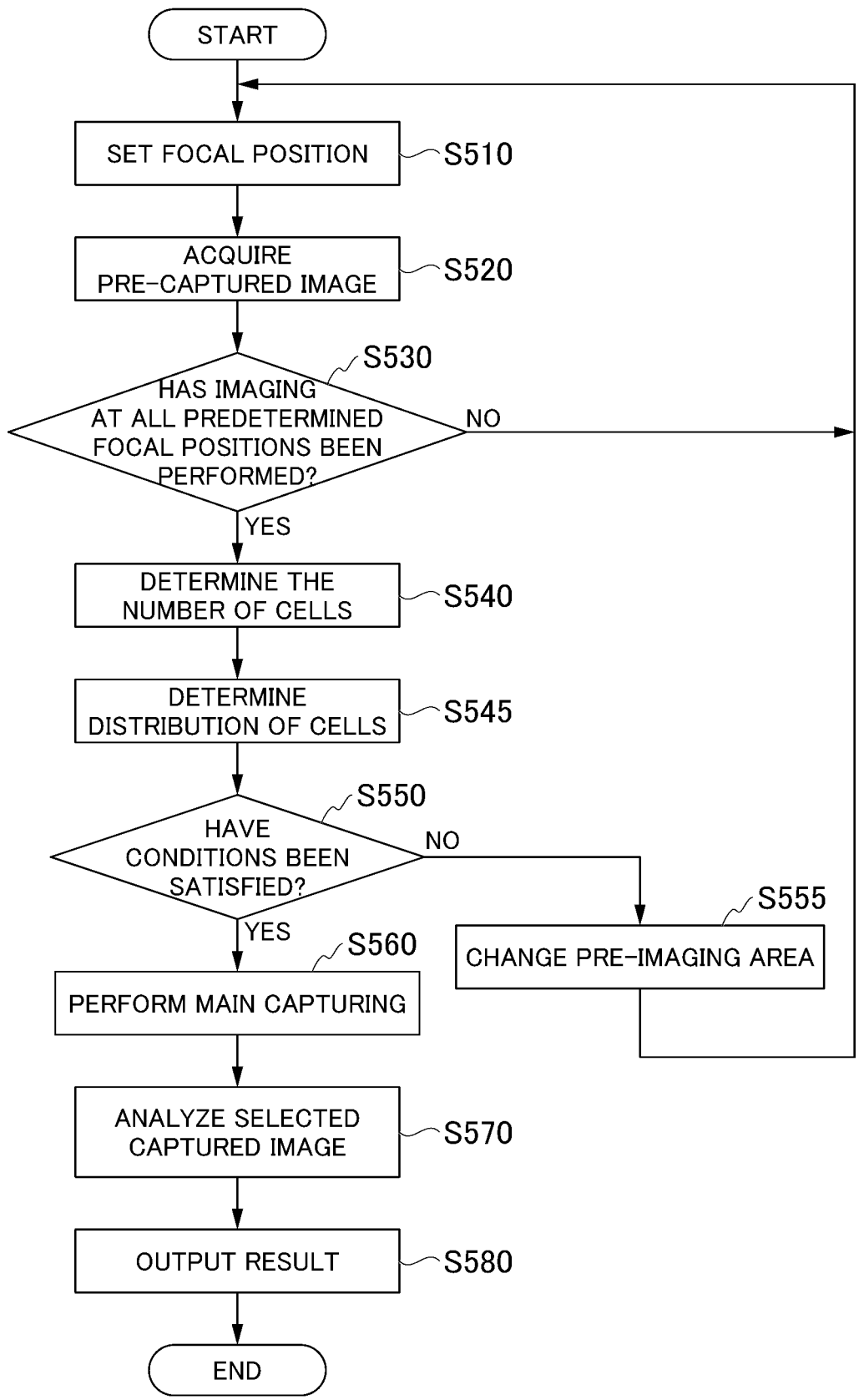
FIG. 6 is a flowchart illustrating an example of this imaging process according to this embodiment.

FIG. 6 is a flowchart illustrating an example of a main capturing process according to this embodiment. The operation process illustrated here is an example, and an operation sequence may be omitted, or an operation sequence may be added.

The control signal outputting unit 500 set a focal position of the objective lens 23 (Step S510). In this embodiment, a plurality of focal positions are stored in the storage unit 200. The focal position set in Step S510 is one of the plurality of focal positions stored in advance in the storage unit 200. For example, the focal positions stored in the storage unit 200 are part of a range in the Z-axis direction that can be driven by the objective lens driving unit 24. The control signal outputting unit 500 supplies a control signal for moving the objective lens 23 to a predetermined focal position to the objective lens driving unit 24. The objective lens driving unit 24 drives the objective lens 23 to a predetermined focal position acquired from the result outputting unit 300. The imaging unit 22 captures a pre-captured image at this predetermined focal position.

The cell image acquiring unit 101 acquires a captured image that is captured at the focal position set by the control signal outputting unit 500 (Step S520). More specifically, the cell image acquiring unit 101 acquires a pre-captured image that has been captured at the predetermined focal position by the imaging unit 22.

The control signal outputting unit 500 determines whether or not imaging at all the predetermined focal positions has been performed (Step S530).

In a case in which it is determined that imaging at all the predetermined focal positions has not been performed (No in Step S530), the control signal outputting unit 500 repeats the process starting from Step S510. More specifically, the analysis device 10 repeats the Steps S510 to S530, thereby acquiring a plurality of pre-captured images of which focal positions are different from each other.

The cell image acquiring unit 101 supplies a plurality of pre-captured images acquired from the imaging unit 22 and focal positions at which these pre-captured images have been captured in a state being associated with each other to the determination unit 102. The determination unit 102 acquires a plurality of pre-captured images from the cell image acquiring unit 101. The cell number calculating unit 121 determines the number of cells for each pre-captured image acquired from the cell image acquiring unit 101 (Step S540). The cell distribution calculating unit 122 determines a distribution of cells for each pre-captured image acquired from the cell image acquiring unit 101 (Step S545).

The determination unit 102 determines whether or not imaging conditions are satisfied for each pre-captured image on the basis of the number of cells calculated by the cell number calculating unit 121 and the distribution of the cells calculated by the cell distribution calculating unit 122 (Step S550).

In a case in which it is determined that the pre-captured image does not satisfy the imaging conditions (No in Step S550), the determination unit 102 selects a pre-imaging area that has not been pre-captured from among a plurality of pre-imaging areas selected in Step S40 described above. The determination unit 102 changes the pre-imaging area to the selected pre-imaging area and repeats the process starting from Step S510 (Step S555).

In a case in which the determination unit 102 determines that the pre-captured image satisfies the imaging conditions (Yes in Step S550), the determination unit 102 supplies a result of the determination to the selection unit 103. The selection unit 103 acquires the result of the determination from the determination unit 102. The selection unit 103 selects an area to be imaged at the time of main capturing on the basis of a plurality of pre-captured images for which the result of the determination acquired from the determination unit 102 indicates that the imaging conditions are satisfied. The selection unit 103, for example, selects a field of vision in which a pre-captured image of which total luminance is high or a pre-captured image having a high area occupancy ratio of cells among a plurality pre-captured images as a field of vision in which main capturing is performed. In accordance with this, the selection unit 103 can select a field of vision in which a field of vision that is more appropriate for an analysis has been imaged among fields of vision satisfying the imaging conditions as a field of vision in which main capturing is performed. The selection unit 103 moves the objective lens 23 to the position of the selected field of vision through the control signal outputting unit 500.

The microscope device 20 captures a main captured image in the field of vision selected by the selection unit 103 (Step S560).

The cell image acquiring unit 101 acquires a main captured image from the imaging unit 22. The cell image acquiring unit 101 supplies the main captured image acquired from the imaging unit 22 to the analysis unit 104. The analysis unit 104 acquires the main captured image from the cell image acquiring unit 101. The analysis unit 104 analyzes the main captured image acquired from the cell image acquiring unit 101 (Step S570). The analysis unit 104 supplies a result of the analysis to the result outputting unit 300. The result outputting unit 300 causes the display unit 30 to display the result of the analysis supplied from the analysis unit 104 (Step S580).

In other words, the analysis device 10 also selects a field of vision in the Z-axis direction on the XY-axes plane in Step S50 in addition to a field of vision of the XY-axes plane selected by the area selecting unit 105.

Here, a difference in the luminance levels of cells will be described with reference to FIG. 7.

Figure 7:
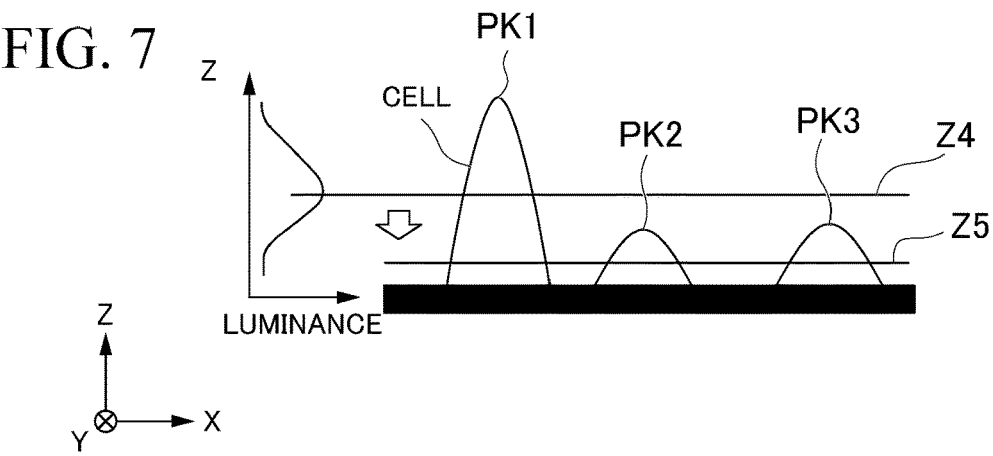
FIG. 7 is a diagram illustrating an example of differences in luminance levels of three cells.

FIG. 7 is a diagram illustrating an example of differences in luminance levels of three cells.

A cell having a peak PK1 has a luminance level of a cell nucleus during cell division. Each of the cells having peaks PK2 and PK3 has a luminance level of a cell nucleus not during cell division. Fluorescence stronger than that of a cell nucleus not during cell division is emitted from a cell nucleus during cell division. When a field of vision in which main capturing is performed is selected on the basis of information of the intensity of fluorescence imaged in the cell image, there are cases in which many cells during cell division are imaged. More specifically, there are cases in which a cell image in which a face of a position Z4 in the Z-axis direction that is out of focus of a cell not during cell division has been imaged is captured. In such cases, the accuracy of the analysis is reduced.

By selecting a field of vision on the basis of the number of cells, the analysis device 10, for example, can select a field of vision in which a face that is also in-focus of a cell not during cell division, like a position Z5 in the Z-axis direction, has been imaged.

Method of Calculating Number of Cells and Distribution of Cells

Here, an example of the process of the determination unit 102 calculating the number of cells and a distribution of the cells will be described with reference to FIGS. 8 and 9. The operation process illustrated here is an example, an operation sequence may be omitted, or an operation sequence may be added.

Figure 8:
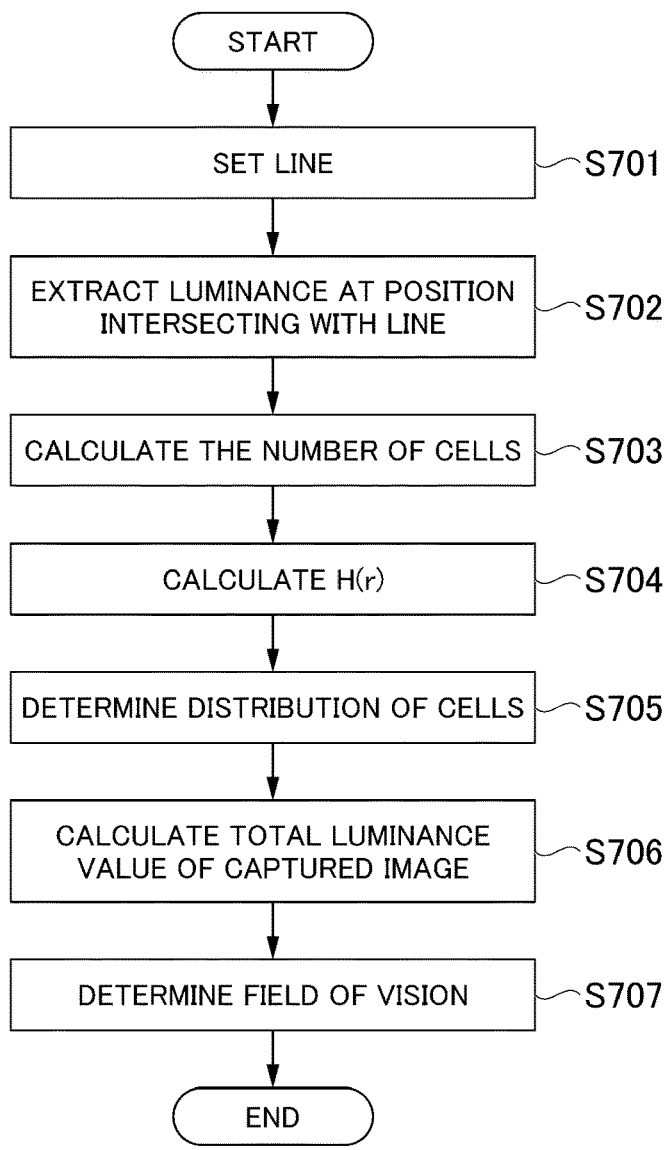
FIG. 8 is a flowchart illustrating an example of an operation process of a determination unit.

FIG. 8 is a flowchart illustrating an example of an operation process of the determination unit 102.

Figure 9:
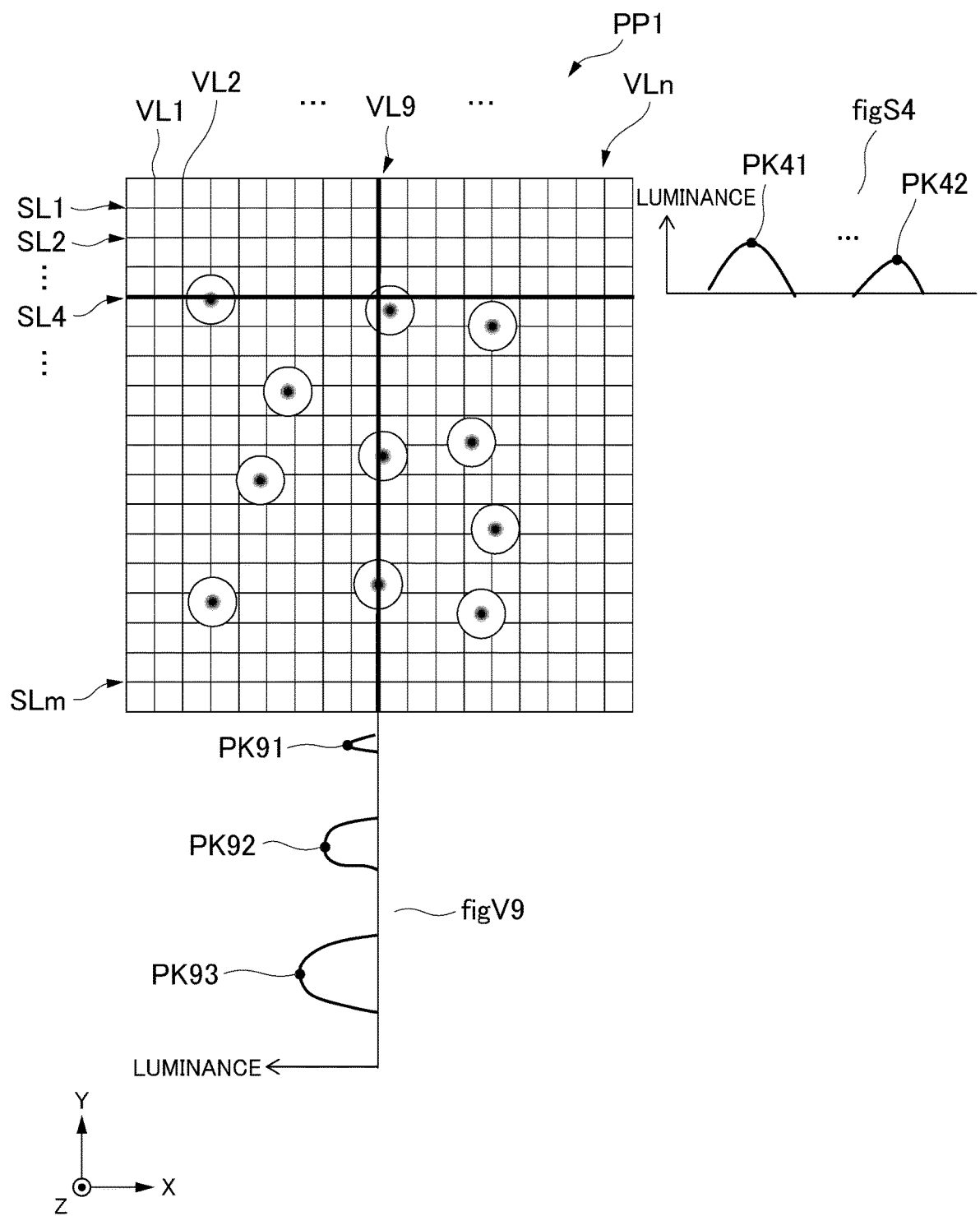
FIG. 9 is a diagram illustrating an example of a line profile.

FIG. 9 is a diagram illustrating an example of a line profile.

Calculation of Number of Cells using Line Profile

The determination unit 102 calculates the number of cells and a distribution of the cells by determining whether or not a cell is imaged at predetermined positions in a pre-captured image PP1. In this embodiment, the predetermined positions are positions at which a plurality of horizontal lines set at a predetermined interval in the horizontal direction of the pre-captured image PP1 and a plurality of vertical lines set at a predetermined interval in the vertical direction of the pre-captured image PP1 intersect with each other. More specifically, the determination unit 102 calculates the number of cells imaged in the pre-captured image PP1 and a distribution of the cells on the basis of luminance levels of pixels disposed at positions intersecting with a line. In the following description, this determination method will be also referred to as a line profile.

The determination unit 102 sets the line described above in the pre-captured image PP1 (Step S701). The line is a line of one pixel in the vertical direction and the horizontal direction of the pre-captured image PP 1. The determination unit 102 sets a plurality of such lines with a predetermined gap interposed therebetween in the vertical direction and the horizontal direction.

More specifically, the determination unit 102, as illustrated in FIG. 9, sets lines from a vertical line VL1 to a vertical line VLn with a predetermined gap interposed therebetween in the X-axis direction. Here, "n" included in the vertical line VLn is an integer that is equal to or larger than one. In the following description, in a case in which the vertical lines VL1 to VLn do not need to be identified from each other, they will be also referred to as vertical lines VL.

In addition, as illustrated in FIG. 9, the determination unit 102 sets lines from horizontal lines SL1 to SLm with a predetermined gap interposed therebetween in the Y-axis direction. "m" included in the vertical line SLm is an integer that is equal to or larger than one. In the following description, in a case in which the horizontal lines SL1 to SLm do not need to be identified from each other, they will be also referred to as horizontal lines SL.

In this embodiment, the predetermined gap is approximately half of a length of the diameter of cell nucleuses included in cells imaged in the pre-captured image PP1. The length of the predetermined gap may be stored in advance in the storage unit 200 or may be set by a user. By setting the predetermined gaps between the vertical lines VL and between the horizontal lines SL set in the line profile to half of a length of the diameter of cell nucleuses, the determination unit 102 can inhibit omission of identification of cells and can identify cells at a high speed.

The determination unit 102 extracts luminance levels at positions at which the lines intersect with each other (Step S702). More specifically, the cell number calculating unit 121 extracts luminance levels of pixels disposed at intersection positions for each vertical line VL and each horizontal line SL. A graph figV9 is a graph acquired by extracting luminance levels of pixels at positions intersecting with the vertical line VL9. A graph figS4 is a graph acquired by extracting luminance levels of pixels at positions intersecting with the horizontal line SL4.

The determination unit 102 calculate the number of cells (Step S703). More specifically, the cell number calculating unit 121 calculates the number of peaks of the extracted luminance levels of pixels. For example, the determination unit 102 calculates the number of cells positioned at the vertical line VL9 as being three on the basis of peaks PK91, PK92, and PK93. In addition, the determination unit 102 calculates the number of cells positioned at the horizontal line SL4 as being two on the basis of peaks PK41 and PK42.

The determination unit 102 may perform the determination by assuming that cell nucleuses are away from each other in accordance with cytoplasm. In such a case, a point to which a peak of the line profile is close is regarded as one cell nucleus in the determination.

Calculation of Distribution of Cells using Line Profile

Next, the determination unit 102 calculates a distribution of cells imaged in the pre-captured image (Step S704). More specifically, the cell distribution calculating unit 122 calculates a distribution of cells through a space analysis. The space analysis is a method of quantitatively analyzing whether points are concentrated or distributed in a spatial range. For example, in the space analysis, Repley's K-Function, H-function acquired by standardizing the K-Function, and the like are used. Such a space analysis, for example, is described in "Biophysical Journal Volume 97 August 2009 1095-1103".

In this embodiment, the cell distribution calculating unit 122 performs a space analysis using the H-Function. In the following description, a score of the space analysis calculated using the H-Function will be also referred to as H(r). Here, r represents a radius from a predetermined position.

The determination unit 102 determines a distribution of cells imaged in the pre-captured image PP on the basis of a result of a space analysis calculated by the cell distribution calculating unit 122 (Step S705).

Here, an example of a result of the space analysis calculated by the cell distribution calculating unit 122 will be described with reference to FIG. 10.

Figure 10:
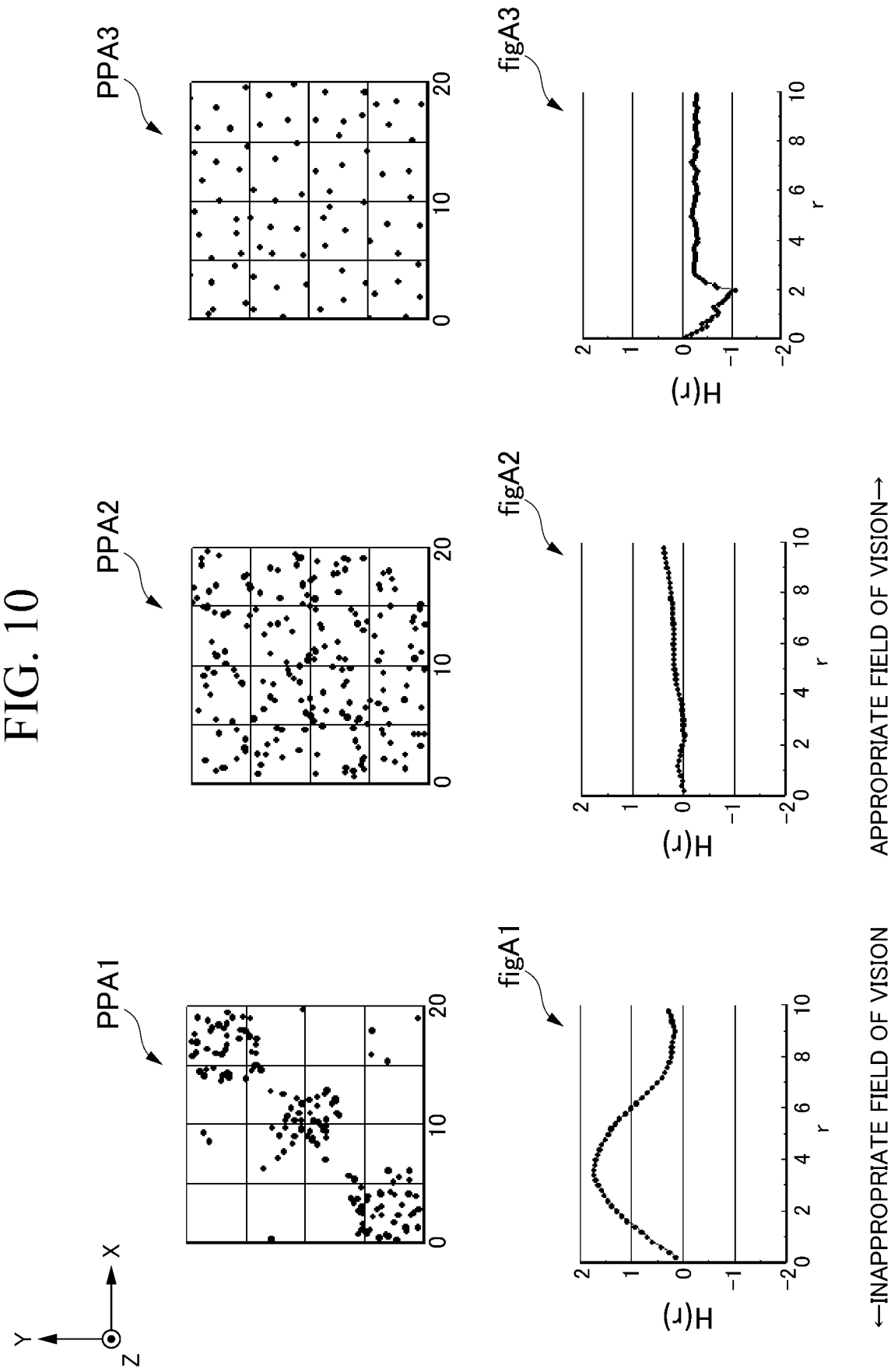
FIG. 10 is a diagram illustrating an example of a result of a space analysis calculated by a cell distribution calculating unit.

FIG. 10 is a diagram illustrating an example of a result of the space analysis calculated by the cell distribution calculating unit 122.

Each of graphs figA1 to figA3 is a graph having a distance from a point disposed at a horizontal axis and a score H(r) of the space analysis. Here, r represents a distance from a predetermined position and represents a circle of a distance having the predetermined position as its center.

The graph figA1 is a result of a space analysis of a pre-captured image PPA1 using the cell distribution calculating unit 122. The pre-captured image PPA1 is a case in which cells form several concentrated spots. When cells form concentrated spots, a probability of another point being present next to a certain point becomes high, and thus the H function represents a value that is equal to or larger than "0". Here, the determination unit 102 determines that a distribution of cells is a distribution that is more appropriate for an analysis as the number of points of which the score H(r) in the graph figA1 is plotted as being equal to or smaller than 0 becomes larger. In this example, the cell distribution calculating unit 122 determines that the pre-captured image PPA1 as not being a distribution that is appropriate for an analysis.

The graph figA2 is a result of a space analysis of a pre-captured image PPA2 using the cell distribution calculating unit 122. The pre-captured image PPA2 is a case in which cells are randomly distributed. Since there are many points of which the score H(r) in the graph figA2 is close to 0, the determination unit 102 determines that the distribution of the cells imaged in the pre-captured image PPA2 is a distribution that is appropriate for an analysis. In this embodiment, since H(r) has a value smaller than 1 in a case in which r is changed, and accordingly, the graph figA2 can be determined as being a distribution that is appropriate for an analysis. H(r) determined as being a distribution that is appropriate for an analysis is not limited to a value smaller than 1. In addition, for example, in a case in which a distribution that is appropriate for an analysis is determined, H(r) entering within a predetermined range, for example, in the range of 1 to 0 may be used.

The graph figA3 is a result of a space analysis of a pre-captured image PPA3 using the cell distribution calculating unit 122. In the pre-captured image PPA3, cells are distributed to exclude other cells. The pre-captured image PPA3 is a case in which cells are uniformly distributed. This is a case in which cells are distributed such that the other cells are not disposed within a radius of 2 from a predetermined cell. Thus, in the range of the distance r up to about 2, the value of H(r) decreases. Since there are many points at which the score H(r) in the graph figA3 is plotted as being equal to or smaller than 0, the determination unit 102 determines that the distribution of cells imaged in the pre-captured image PPA3 is a distribution that is appropriate for an analysis.

In a case in which the graphs figA2 and figA3 are compared with each other, when the scores H(r) are compared with each other, a more appropriate field of vision is determined when the number of points plotted as being equal to or smaller than "0" becomes larger. Therefore, the graph figA3 having a smaller number of values that are equal to or smaller than 0 out of the graphs figA2 and figA3 is determined by the determination unit 102 as being a more appropriate field of vision on the basis of H(r). In this embodiment, although the determination unit 102 determines a more appropriate field of vision as the number of points of H(r) plotted as being equal to or smaller than "0" becomes larger, the determination criterion is not limited thereto, and, for example, the graph figA2 having a smaller number of positive values out of the graphs figA1 and figA2 is determined as being a more appropriate field of vision by the determination unit 102 on the basis of H(r).

The determination unit 102 supplies pre-captured images for which the number of cells calculated by the cell number calculating unit 121 and the distribution of the cells calculated by the cell distribution calculating unit 122 satisfy imaging conditions to the selection unit 103.

The selection unit 103 acquires pre-captured images satisfying the imaging conditions from the determination unit 102. The selection unit 103 calculates a total luminance value for each of the acquired pre-captured images (Step S706).

The selection unit 103 determines a field of vision on the basis of the calculated total luminance values (Step S707). More specifically, the selection unit 103 selects an image captured with a field of vision having better imaging conditions among a plurality of images of which results of determination indicate that the imaging conditions are satisfied. The selection unit 103 selects the field of vision in which the selected image has been captured as a field of vision for main capturing.

SUMMARY

As described above, the analysis device 10 includes the determination unit 102. The determination unit 102 calculates the number of cells images in pre-captured images and a distribution of the cells. The determination unit 102 determines a field of vision of the pre-captured image on the basis of the results of calculation of the number of the cells and the distribution of the cells. The selection unit 103 selects a field of vision that is more appropriate for main capturing on the basis of pre-captured images for which the results of determination acquired by the determination unit 102 satisfy the imaging conditions. In accordance with this, the analysis device 10 can select a field of vision in which the direction of the XY plane and the Z-axis direction are appropriate for main capturing. In addition, by including the control signal outputting unit 500, the analysis device 10 can cause the microscope device 20 to capture a main captured image having the selected field of vision that is appropriate for main capturing.

In addition, the analysis device 10 includes the area selecting unit 105. The area selecting unit 105 cuts out an area in a field of vision corresponding to a high-magnification image from a low-magnification image, thereby determining the number and a distribution of cells. In accordance with this, the analysis device 10 can select a pre-imaging area on the XY plane at a high speed.

In addition, in the description presented above, although the analysis device 10 has been described to be configured to include the area selecting unit 105, the area selecting unit 105 is not essential. By including the area selecting unit 105, the analysis device 10 can select an area in which a high-magnification image is captured from a low-magnification image. In accordance with this, when compared to a configuration not including the area selecting unit 105, the analysis device 10 can acquire a cell image in which the number of cells and the distribution of the cells are appropriate for an analysis for a smaller number of times of capturing. Since the analysis device 10 can acquire a cell image that is appropriate for an analysis for a smaller number of times of capturing, a cell image used for an analysis can be acquired in a short time.

In addition, since the analysis device 10 can decrease the number of times of capturing a pre-captured image that is necessary for selection of a field of vision, the luminance level of fluorescence of cells that are fluorescence-stained can be maintained. In a case in which a cell image is captured, the microscope device 20 emits excitation light to cells that are fluorescence-stained and images the fluorescence that is excited by the excitation light. Since the microscope device 20 images cells a plurality of number of times, the luminance level of fluorescence generated from the cells to which the excitation light has been emitted decreases. When the luminance level of fluorescence decreases, there are cases in which the accuracy of the analysis of cells becomes low. In other words, by including the area selecting unit 105, the analysis device 10 can analyze cells with high accuracy.

In the description presented above, although a case in which the area selecting unit 105 selects an area of an XY plane that is a plane orthogonal to the optical axis of the objective lens 23 has been described, the present invention is not limited thereto. The area selecting unit 105 may select an area in the Z-axis direction that is a direction parallel to the optical axis of the objective lens 23.

In the description presented above, although a configuration in which the cell image acquiring unit 101 acquires a captured image from the microscope device 20 has been described, the present invention is not limited thereto. The cell image acquiring unit 101 may acquire a captured image from a personal computer, a storage device, or the like in which a captured image that has been captured in advance and a field of vision in which this captured image has been captured are stored in the state of being associated with each other. In addition, the microscope device 20 may be configured to include the analysis device 10.

In the description presented above, although a configuration in which the determination unit 102 calculates the number of cells and a distribution of the cells using a line profile has been described, the present invention is not limited thereto. For example, the determination unit 102 may determine the number of cells and a distribution of the cells on the basis of luminance levels of pixels at positions set in advance without being limited to the vertical lines VL and the horizontal lines SL of the pre-captured image PP1.

In the description presented above, although a configuration in which the determination unit 102 determines the number of cells and a distribution of the cells using luminance values at predetermined positions in the pre-captured image has been described, the present invention is not limited thereto. The determination unit 102 may determine the number of cells and a distribution of the cells on the basis of a reference image stored in the reference image storing unit 202. In such a case, the determination unit 102 determines whether or not imaging conditions are satisfied by performing image processing of the reference image and the pre-captured image PP.

Figure 11:
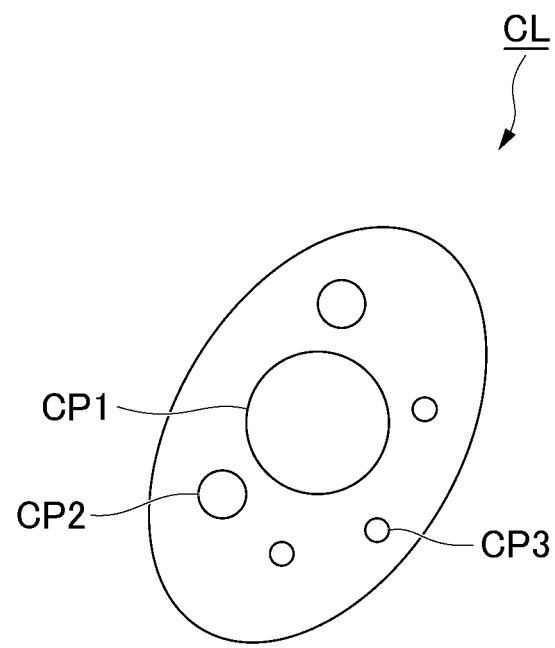
FIG. 11 is a diagram illustrating an example of constituent elements of a cell.

In the description presented above, although a configuration in which the determination unit 102 identifies cells CL on the basis of cell nucleuses has been described, the present invention is not limited thereto. For example, as illustrated in FIG. 11, the determination unit 102 may identify cells CL on the basis of a constituent element CP2 of cells or a constituent element CP3 of cells other than the cell nucleus CP1. Here, in the constituent elements of cells, small cellular organs (organelles) such as a cell nucleus, a lysosome, a Golgi body, and mitochondria, a protein configuring the organelles, an aggregate of proteins, and the like are included.

FIG. 11 is a diagram illustrating an example of constituent elements of a cell CL.

In the description presented above, although a configuration in which the determination unit 102 identifies cells on the basis of luminance levels of cell nucleuses has been described, the present invention is not limited thereto. The determination unit 102 may determine a captured image by calculating the number of cells and a distribution of the cells on the basis of shapes of constituent elements of cells imaged in the pre-captured image. More specifically, the determination unit 102 can detect cytoplasm, an aggregate, and the like. For example, there are cases in which a nucleus of a cell is incorrectly recognized due to a short distance between nucleuses of cells adjacent to each other. In such cases, in a case in which the determination unit 102 determines a cell in accordance with an aggregate of cells, the analysis device 10 can determine the number of cells and a distribution of the cells with higher accuracy. In addition, since the determination unit 102 can detect an aggregate, cells including aggregates can be extracted from among a plurality of cells. In other words, for example, cells can be selected with cells including aggregates specified among imaged cells, and the analysis device 10 can determine the number of selected cells and a distribution of the cells.

In the description presented above, although a case in which a field of vision for main capturing is selected by the selection unit 103 has been described, the present invention is not limited thereto. A field of vision for main capturing may be selected by a user. In such a case, the determination unit 102 causes the display unit 30 to display pre-captured images satisfying the imaging conditions. A user selects an image in which a desired field of vision has been imaged from among pre-captured images displayed on the display unit 30 by operating the operation unit 40. The selection unit 103 may acquire an operation of selecting an image in which a field of vision desired by a user has been captured from the operation detecting unit 400 and select the field of vision imaged in the pre-captured image selected by the user as a field of vision for main capturing.

In the embodiment described above, although the number of cells in a captured cell image is calculated, instead of the number of cells, a ratio of a cell area occupied in a captured cell image may be calculated. The ratio of the cell area, for example, is a ratio between an area in which a cell has been imaged and an area in which no cell has been imaged inside the cell image. The determination unit 102, for example, determines that the number of cells is large for a cell image having a higher ratio of the area occupied by cells than a cell image having a low ratio of the area occupied by cells.

In the embodiment described above, in a case in which an area in which an image used for an analysis is captured is selected, appropriateness/inappropriateness of an analysis is reviewed from an image captured under the first imaging conditions, and an analysis is performed using an image captured under the second imaging conditions after a field of vision is selected. As the first imaging conditions and the second imaging conditions, there is an imaging magnification, and a first imaging magnification is lower than a second imaging magnification. The first imaging conditions and the second imaging conditions may be the same. The present invention is not limited to such a case, and, in a case in which an image captured under the first imaging conditions is an image that is appropriate for an analysis, the analysis may be performed using the image. In other words, an image for selecting a field of vision that is appropriate for an analysis and an image used for an analysis may be either the same or different from each other.

By recording a program for executing each process of the analysis device 10 according to the embodiment of the present invention in a computer-readable recording medium and causing a computer system to read and execute the program recorded in this recording medium, various processes described above may be performed.

The "computer system" described here includes an operating system (OS) and hardware such as peripherals. In addition, in a case in which a WWW system is used, "computer system" also includes a home page providing environment (or a display environment). Furthermore, the "computer-readable recording medium" represents a writable nonvolatile memory such as a flexible disk, a magneto-optical disk, a ROM, or a flash memory, a portable medium such as a CD-ROM, or a storage device such as a hard disk built into the computer system.

In addition, the "computer-readable recording medium" includes a medium storing the program for a predetermined time such as an internal volatile memory (for example, a Dynamic Random Access Memory (DRAM)) of a computer system serving as a server or a client in a case in which the program is transmitted through a network such as the Internet or a communication line such as a telephone line. In addition, the program described above may be transmitted from a computer system storing this program in a storage device or the like to another computer system through a transmission medium or a transmission wave in a transmission medium. Here, the "transmission medium" transmitting a program represents a medium having an information transmitting function such as a network (communication network) including the Internet and the like or a communication line (communication wire) including a telephone line. The program described above may be used for realizing a part of the functions described above. In addition, the program described above may be a program realizing the functions described above by being combined with a program recorded in the computer system in advance, a so-called a differential file (differential program).

As above, although the embodiment of the present invention has been described in detail with reference to the drawings, a specific configuration is not limited to this embodiment, and a design and the like in a range not departing from the concept of the present invention are included therein.

In addition, the requirements of the embodiments described above may be appropriately combined. In addition, some constituent elements may be configured not to be used. As long as permitted by laws and ordinances, disclosure of all the published official gazettes and U.S. Patents relating to devices and the like cited in each embodiment and the modified examples described above are incorporated herein by reference.

REFERENCE SIGNS LIST

1 Microscope observation system
10 Analysis device
20 Microscope device
30 Display unit
101 Cell image acquiring unit
102 Determination unit
103 Selection unit
104 Analysis unit 105 Area selecting unit
200 Storage unit
300 Result outputting unit
400 Operation detecting unit

The invention claimed is:

1. An image-processing device comprising:
a processor programed to
a determination unit configured to determine perform a determination with respect to a captured image on the basis of (a) at least one selected from the group of the number of cells and a ratio of cell area and (b) a distribution of the cells in the captured image acquired by imaging a sample including a plurality of cells; and
set an area used for analyzing the cells on the basis of a result of the determination.

2. The image-processing device according to claim 1, wherein the processor is programed to calculate (a) at least one selected from the group of the number of cells and the ratio of cell area and (b) the distribution of the cells on the basis of cell nucleuses in the cells imaged in the captured image.

3. The image-processing device according to claim 1, wherein resolution of the captured image is lower than that of an image used for the analysis of the cells.

4. The image-processing device according to claim 1, wherein the processor is programed to calculate (a) at least one selected from the group of the number of cells and the ratio of cell area and (b) the distribution of the cells by determining whether or not the cells are at predetermined positions in the captured image.

5. The image-processing device according to claim 4, wherein the predetermined positions are positions at which a plurality of straight lines set at a predetermined interval in a first direction of the captured image and a plurality of straight lines set at the predetermined interval in a vertical direction to the first direction of the captured image intersect with each other.

6. The image-processing device according to claim 5, wherein the predetermined interval is approximately half of a length of a diameter of the cell nucleuses in the captured image.

7. The image-processing device according to claim 1, wherein the processor is programed to calculate (a) at least one selected from the group of the number of cells and the ratio of cell area and (b) the distribution of the cells on the basis of shapes of constituent elements of the cells in the captured image.

8. The image-processing device according to claim 1, wherein
the captured image is a captured image captured with an imaging magnification lower than a magnification of an image used for the analysis, and
the processor is further programmed to select candidates for an area in which an image used for the analysis is captured by calculating, for the captured image, (a) at least one selected from the group of the number of cells and the ratio of cell area and (b) the distribution of the cells for each imaging range according to an imaging magnification of the image used for the analysis.

9. The image-processing device according to claim 1, wherein the processor is further programmed to acquire a plurality of the captured images in different fields of vision.

10. The image-processing device according to claim 9, wherein the processor is programed to receive the captured image from another device capturing the captured image.

11. The image-processing device according to claim 9,
wherein the captured image is captured through an objective lens, and
wherein the different fields of vision are different along an optical axis of the objective lens.

12. The image-processing device according to claim 9,
wherein the captured image is captured through an objective lens, and
wherein the different fields of vision are different along a plane that is orthogonal to an optical axis of the objective lens.

13. The image-processing device according to claim 1, wherein the processor is programed to determine whether or not the captured image is appropriate for the analysis of the cells.

14. An image-processing method comprising:
determining a captured image on the basis of (a) at least one selected from the group of the number of cells and a ratio of cell area and (b) a distribution of the cells in the captured image acquired by imaging a sample including a plurality of cells; and
setting an area used for analyzing the cells on the basis of a result of the determination acquired in the determining of the captured image.

15. A non-transitory computer readable medium storing thereon an image-processing program causing a computer to execute:
determining a captured image on the basis of (a) at least one selected from the group of the number of cells and a ratio of cell area and (b) a distribution of the cells in the captured image acquired by imaging a sample including a plurality of cells; and
setting an area used for analyzing the cells on the basis of a result of the determination acquired in the determining of the captured image.

* * * * *